(12) United States Patent
King et al.

(10) Patent No.: US 8,491,878 B2
(45) Date of Patent: Jul. 23, 2013

(54) SANITIZING FORMULATION

(75) Inventors: Simon King, Weybridge (GB); Madhu Parmar, Weybridge (GB); Kimberly Biedermann, Parsippany, NJ (US); Philip Oths, Parsippany, NJ (US)

(73) Assignee: Glaxo Group Limited, Greenford, Middlesex (GB)

( * ) Notice: Subject to any disclaimer, the term of this patent is extended or adjusted under 35 U.S.C. 154(b) by 442 days.

(21) Appl. No.: 12/353,280

(22) Filed: Jan. 14, 2009

(65) Prior Publication Data

US 2009/0208444 A1     Aug. 20, 2009

(30) Foreign Application Priority Data

Jan. 16, 2008 (GB) .................................. 0800788.2

(51) Int. Cl.
*A61K 31/74* (2006.01)

(52) U.S. Cl.
USPC ...................................................... 424/78.08

(58) Field of Classification Search
None
See application file for complete search history.

(56) References Cited

U.S. PATENT DOCUMENTS

| | | | |
|---|---|---|---|
| 3,141,821 A | 7/1964 | Compeau et al. | |
| 4,404,040 A | 9/1983 | Wang | |
| 4,514,385 A | 4/1985 | Damani et al. | |
| 4,664,835 A | 5/1987 | Grollier et al. | |
| 6,109,675 A | 8/2000 | Sumrall | |
| 6,146,622 A | 11/2000 | Castillo et al. | |
| 6,287,577 B1 | 9/2001 | Beerse et al. | |
| 2004/0048755 A1* | 3/2004 | Lopes | 510/111 |
| 2004/0171507 A1* | 9/2004 | Kellar et al. | 510/367 |
| 2005/0049172 A1 | 3/2005 | Lukenbach et al. | |
| 2005/0159321 A1* | 7/2005 | Cusack et al. | 510/108 |
| 2005/0271717 A1 | 12/2005 | Berchielli et al. | |
| 2006/0094610 A1 | 5/2006 | Yamato et al. | |
| 2007/0280901 A1 | 12/2007 | Fuls et al. | |
| 2008/0132438 A1* | 6/2008 | Hoffman et al. | 510/380 |

FOREIGN PATENT DOCUMENTS

| | | |
|---|---|---|
| EP | 0997525 | 5/2000 |
| EP | 1090631 A1 | 4/2001 |
| EP | 1090631 | 11/2001 |
| EP | 1510204 | 3/2005 |
| GB | 2393908 A | 4/2004 |
| WO | WO98/12294 | 3/1998 |
| WO | WO99/24012 | 5/1999 |
| WO | WO 9924012 A1 | 5/1999 |
| WO | WO 2004101724 A1 | 11/2004 |
| WO | WO 2004101725 A1 | 11/2004 |
| WO | WO 2005004663 A1 | 1/2005 |
| WO | WO2005/087185 | 9/2005 |
| WO | WO 2005110357 A2 | 11/2005 |
| WO | WO 2005110357 A3 | 11/2005 |

* cited by examiner

*Primary Examiner* — Paul Dickinson

(74) *Attorney, Agent, or Firm* — Joshua C. Sanders; Theodore R. Furman

(57) ABSTRACT

A sanitizing formulation comprising a solution of an acidic polymer and an anionic surfactant in a liquid vehicle. Suitable acidic polymers are those which include adjacent

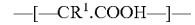

units where $R^1$ is defined in their structure, for example polymers based on maleic acid moieties which typically include —[—CH.COOH—CH.COOH—]— units, such as known Gantrez™ polymers. A suitable anionic surfact is sodium lauryl sulphate.

10 Claims, No Drawings

SANITIZING FORMULATION

FIELD OF THE INVENTION

This invention relates to sanitising formulations, in particular for cleaning human skin such as the hands, having activity against harmful micro-organisms such as bacteria and viruses.

BACKGROUND OF THE INVENTION

Hand hygiene has risen in importance in recent years in response to the increased incidence of infection in hospitals by such resistant organisms as MRSA, and in recognition of publicized incidents of infection in closed communities such as cruise liners. In hospitals a common route of transmission of such organisms is via the hands of health care workers. The World Health Organisation (WHO) has produced guidelines on hand hygiene: "*WHO Guidelines on Hand Hygiene in Healthcare*" Advanced Draft 2007 (referred to herein as WHO Guidelines). According to the WHO Guidelines, human skin is populated by two broad categories of microorganisms, namely resident and transient. Resident organisms reside under the superficial cells of the stratum corneum, and also on the surface of the skin. *Staphylococcus epidermis* is the dominant species. In general resident organisms are less likely to be associated with infections but may cause infections in sterile body cavities, in the eyes or on non-intact skin. Transient organisms which colonise the superficial layers of skin are the organisms most frequently associated with health care associated infections, and common transient microorganisms are for example *S. aureus*, other Staphylococci, *Clostridium difficile, E. coli* and various viruses such as rotavirus, influenza viruses and rhinovirus.

As a response to transmission and cross-contamination of microorganisms by persons with infected hands such as hospital care workers, efficient washing of local inanimate surfaces such as furniture and workers' hands using a sanitising formulation is the most common proposed solution. Such sanitizing formulations are generally in the form of mobile liquids or gels which can be conveniently applied to such surfaces, suitable viscosities for such formulations being well known in the field. Numerous sanitising formulations are known for example as disclosed in WO-A-2004/101724, WO-A-2004/101725 and WO-A-2005/110357 being typical examples. Some known sanitizing formulations are based on combinations of surfactants, such as sodium lauryl sulphate, and certain acidic polymers such as so called Carbopol. Such formulations are for example disclosed in WO-A-1999/24012, GB-A-2 393 908, EP-A-1 090 631 and WO-A-2005/04663.

The WHO Guidelines also list numerous substances which have been used for hand sanitising in an attempt to decontaminate skin from harmful organisms, including soaps, alcohols, chlorhexidine, chloroxylenol, hexachlorophene, iodine, iodophors, quaternary ammonium compounds, triclosan, hypochlorites etc. Some of these substances are associated with hazards, for example alcohols are inflammable and iodine and other halogens can be corrosive or release for example free chlorine gas.

It is known for example from applicant's co-pending PCT/EP2007/057298, WO-A-03/039713 and U.S. Pat. No. 7,029,516 that certain acidic polymers have virus deactivating activity and can be deposited onto fibrous substrates for us as air filter systems. It has unexpectedly been discovered that by formulating acidic polymers in specific novel ways sanitising formulations having both anti-viral and anti-bacterial activity may be provided. It is an object of the invention to exploit this discovery in the provision of improved sanitising formulations, for example having improved efficacy, or efficacy against a wider range of microorganisms, or avoiding the disadvantages associated with known sanitising formulations.

SUMMARY OF THE INVENTION

According to a first aspect of this invention a novel sanitising formulation comprises a solution of an acidic polymer and an anionic surfactant in a liquid vehicle.

DETAILED DESCRIPTION OF THE INVENTION

As used herein the term "sanitising" refers to deactivating, by for example killing or otherwise, potentially harmful pathogens such as bacteria or viruses. The sanitising formulations of this invention may additionally have a cleansing action in facilitating the removal of dirt from surfaces.

As used herein the term "acidic polymer" includes a polymer having acidic groups along its backbone, e.g. as side groups. Suitable acidic groups are carboxylic acid groups. The acidic polymer may be cross-linked or linear. Generally for the present application non-cross linked, e.g. linear polymers are preferred. This is inter alia because relative to cross-linked polymers non-cross linked linear structure can provide more available —COOH groups, and also non-cross linked polymers are easier to dissolve and consequently to use in the preparative process disclosed herein.

The acidic polymer may comprise a poly-(carboxylic acid) polymer.

Poly-(carboxylic acid) polymers are typically polymers which include —COOH groups in their structure, or derivative groups such as acid-anhydride groups, readily cleavable carboxylic acid ester groups or salified —COOH groups which readily cleave to yield —COOH groups.

A poly-(carboxylic acid) polymer may have its —COOH groups (or derivative groups) directly linked to its backbone, or the polymer may be a so-called grafted or dendritic polymers in which the —COOH (or derivative) groups are attached to side chains branching off from the backbone.

For example poly-(carboxylic acid) polymers may include:

—[—CR$^1$.COOH—]— units in their structure, wherein R$^1$ is preferably hydrogen, or R$^1$ may be C$_{1-3}$ alkyl, C$_{1-3}$ alkoxy or C$_{1-3}$ hydroxy alkyl.

One type of such a poly-(carboxylic acid) polymer comprises a polymer having units:

—[—CR$^2$R$^3$—CR$^1$.COOH—]— in its structure wherein R$^2$ and R$^3$ are independently preferably hydrogen, or may be C$_{1-3}$ alkyl or C$_{1-3}$ alkoxy. For example such a polymer may comprise a poly-(carboxyvinyl) polymer, for example a polymer of a monomer compound of formula CR$^2$R$^3$=CR$^1$.COOH wherein the substituents are as defined above. Such a polymer may comprise a polymer of acrylic acid or methacrylic acid, i.e. polyacrylic or polymethacrylic acid, e.g. linear polyacrylic and polymethacrylic acid homo- and co-polymers. An example of such a polymer is carboxypolymethylene. An example of a commercially available polyacrylic acid is the material Good-Rite™ K-702 which has a molecular weight of around 30,000. An example of a commercially available polyacrylic acid, as its sodium salt, is the material Good-Rite™ K-765 which also has a molecular weight of around 30,000. Polyacrylic acid polymers are commercially available under the trade name Carbomer™ classified as a synthetic polymer and is otherwise used as an emulsion stabilizer as well as an aqueous viscosity-increasing agent.

Polymers of this type are for example disclosed in U.S. Pat. No. 2,798,053 viz "a carboxylic monomer such as acrylic acid, maleic acid or anhydride and the like, copolymerized with certain proportions of a polyalkenyl polyether of a polyhydric alcohol containing more than one alkenyl ether grouping per molecule, the parent polyhydric alcohol containing at least 4 carbon atoms and at least three hydroxyl groups."

Another type of poly-(carboxylic acid) is a cross-linked poly-(carboxylic acid) polymer. Examples of such include homopolymers of acrylic acid crosslinked with an allyl ether, e.g. of pentaerythritol, of sucrose or of propylene, e.g. the material available from B.F. Goodrich Company under the trade name "Carbopol", such as the specific Carbopols include Carbopol 934, 940, 980, 1382, Carbopol ETD 2020, ETD 2050, Ultrez 20 and 21.

Another type of such a poly-(carboxylic acid) polymer may include adjacent

units (where $R^1$ is defined above) in its structure, for example polymers based on maleic acid moieties which typically include —[—CH.COOH—CH.COOH—]— units, and/or salts or esters of such units, or such units in anhydride form in which COOH groups on adjacent carbon atoms may be cyclised to form a —CH.CO—O—CO.CH— ring system, such derivatives being susceptible to hydrolysis to form the corresponding free acid.

One type of such a poly-(carboxylic acid) polymer may comprise units with pairs of carboxylic acid groups on adjacent polymer chain carbon atoms. For example such polymers may comprise units:

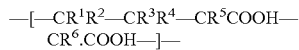

in its structure wherein $R^1$, $R^2$, $R^3$, $R^4$, $R^5$ and $R^6$ are independently hydrogen (preferred) or $C_{1-3}$ alkyl or $C_{1-3}$ alkoxy, preferably $R^1$ and $R^2$ being hydrogen, $R^3$ being hydrogen $R^4$ being methoxy, and $R^5$ and $R^6$ being hydrogen, or a derivative thereof retaining COOH groups in its structure, or groups readily hydrolysable to COOH groups. Such a poly-(carboxylic acid) polymer is the polymer based on a copolymer of methyl vinyl ether and maleic anhydride. Such polymers are commercially available under the trade name Gantrez™.

An example of such a polymer comprises:

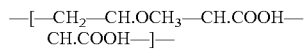

units in its structure.

Such polymers may be linear polymers, or cross linked polymers. Linear, non-cross linked, polymers of this type are commercially available under the trade name Gantrez™ S (CAS #25153-4-69), e.g. Gantrez™ S-96 having a molecular weight ca. 700,000, Gantrez™ S-97 having a molecular weight ca. 1,200,000. Such Gantrez polymers are preferred. Such Gantrez™ polymers are commercially available as aqueous solutions in which form they may be used in the formulations of the present invention.

Cross linked polymers of this type are also commercially available under the Gantrez™ trade name.

An example of a derivative of such an acid is an anhydride, i.e. in which the two adjacent —COOH groups are cyclised to form a

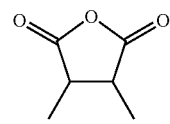

ring system, such an anhydride is susceptible to hydrolysis to form the corresponding free acids. Such polymers are commercially available under the trade name Gantrez™ AN(CAS #9011-16-9), e.g. Gantrez™ AN-119, Gantrez™ AN-903, Gantrez™ AN-139, Gantrez™ AN-169.

Another example of a derivative is a partial salt, e.g. where some of the free —COOH groups are converted into a metal salt of a Group I or Group II metal such as respectively either sodium or calcium, or a mixed sodium-calcium salt. Such a polymer is commercially available under the trade name Gantrez™ MS, e.g. Gantrez™ MS-955 (CAS #62386-95-2).

Another example of a derivative of such an acid is a partial ester in which some of the free —COOH groups are esterified with $C_{1-6}$ alkyl e.g. ethyl or n-butyl. Such polymers are commercially available under the trade name Gantrez™ ES, e.g. Gantrez™ ES-225 (CAS #25087-06-03) or Gantrez™ ES-425 (CAS #25119-68-0. Typically polymers of this second type have molecular weights in the range 200,000-2,000,000.

In the sanitizing formulations of the present invention poly-(carboxylic acid) polymers which include adjacent

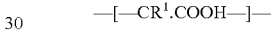

units (where $R^1$ is defined above) in their structure, for example polymers based on maleic acid moieties, such as the above-mentioned Gantrez™ materials are found to have the advantage that because of their viscosity when in combination with the anionic surfactant, they are retained for a longer time on a surface to which they are applied, relative for example to sanitizing formulations of the invention when based on for example the Carbopol™ type materials. This longer retention can result in prolonged activity on the surface. A further advantage of these polymers is that they can flow more easily, can be more easily sprayed, and can get into more confined spaces than for example the sanitizing formulations based on Carbopol™ type acidic polymers.

Other suitable poly-(carboxylic acid) polymers include copolymers of $C_{10-30}$ alkyl acrylates and one or more monomer compound of formula $R^4R^5C\!=\!CR^6\!-\!COOR^7$, wherein each of $R^4$, $R^5$, $R^6$, and $R^7$ is independently selected from hydrogen or $C_{1-5}$ alkyl, in particular methyl, ethyl or propyl. Examples of such monomer compounds include esters of acrylic acid and methacrylic acid.

Other suitable poly-(carboxylic acid) polymers include anionic polymers based on compounds of formula $R_1R_2C\!=\!CR_3\!-\!COOR_4$, wherein each of $R_1$, $R_2$, $R_3$ and $R_4$ is independently selected from hydrogen or $C_{1-5}$ alkyl, in particular methyl, ethyl or propyl. Examples of such polymers are those based on methacrylic acid and ethylacrylates with carboxylic acid functional groups available from Rohm GmbH & Co under the trade name "Eudragit". Specific grades include Eudragit L100-55, L30-D-55, L100, S100 and FS 30D.

Other suitable acidic polymers may be polymers incorporating other acid groups such as sulphonic acid groups. Example of acidic polymers incorporating sulphonic acid groups are co-polymers of an acrylic or methacrylic acid with a sulphonic acid, e.g. linear copolymers. Such polymers incorporating sulphonic acid groups may be used in the form of their salts, e.g. their sodium salts. An example of a copolymer of acrylic acid and sulphonic acid is commercially available under the trade name Good-Rite™ K-776. Other acidic polymers may comprise copolymers of acrylic acid and a sulphonic acid. For example the acidic polymer may comprise copolymers and terpolymers of maleic acid, poly(2-acrylamido-2-methylpropane sulfonic acid) ("polyAMPS"), and copolymers of acrylic acid and 2-acrylamido-2-methyl-propane sulfonic acid.

Polystyrene sulphonic acids may be suitable, for example a commercially available polystyrene sulphonic acid in the form of its sodium salt available under the name Flexan™ II with a molecular weight of around 120,000 may be suitable.

Other suitable acidic polymers are believed to include polyvinyl phosphonic acids.

Acidic polymers which have been found useful for the purposes herein have been found to have molecular weights in the range 30,000 to 2,000,000 but molecular weight does not appear to be critical, and this may be simply an exemplary range.

Preferred acidic polymers are the above-mentioned Carbopol ETD 2020 and Gantrez™ S97.

Typically, anionic surfactants are compounds having a hydrophilic anionic group and an associated cation. Such a cation may be metallic, such as alkali metal, or non-metallic such as ammonium or quaternary ammonium. Typically such anionic surfactants comprise the hydrophilic anionic group and the cation in the form of a salt. Preferably the anionic surfactant comprises a sodium salt of an organic hydrophilic anionic group. Suitably the organic hydrophilic anionic group may be a sulphonic acid or carboxylic acid group.

A preferred such anionic surfactant compound has the formula (I):

$$C_nH_{2n+1}\text{---}Z^-M^+ \quad (I)$$

where n is 8 to 20, preferably 10 to 15, Z is $SO_3$ or $SO_4$, and M is sodium or potassium. A preferred anionic surfactant of this type is sodium lauryl sulphate (n=12, Z is $SO_4$, M is sodium).

Other anionic surfactants which may be suitable are those of the formula (II):

$$C_nH_{2+1}\text{---}X\text{---}C_mH_{2m}\text{---}Z^-M^+ \quad (II)$$

where n+m are 8 to 20, X is —O— or —CO.O—, Z is $SO_3$ or $SO_4$, and M is sodium or potassium. A preferred anionic surfactant of this type is sodium cocoyl isethionate (n=9, m=2, X is CO.O, Z is $SO_3$, M is sodium). Another anionic surfactant of formula (II) is sodium laureth sulphate.

Other anionic surfactants which may be suitable are those of the formula (III):

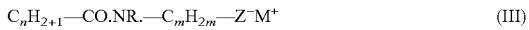

$$C_nH_{2+1}\text{---}CO.NR.\text{---}C_mH_{2m}\text{---}Z^-M^+ \quad (III)$$

Where n and m are each 1 or more, n+m are 8 to 20 R is $C_{1-3}$ alkyl, Z is CO.O, $SO_3$ or $SO_4$, and M is sodium or potassium. Preferred anionic surfactants of this type are sodium lauroyl sarcosinate (n=11, R is methyl, m=1, M is sodium), and sodium methyl cocoyl taurate (R is methyl, m=2, Z is $SO_3$, M is sodium).

Other anionic surfactants are olefin sulphonates such as alpha-olefin sulphates such as the commercial material Bioterge™ As-40, being the sodium salt of $C_{14-16}$ sulphonates.

Other anionic surfactants which may be suitable include sodium methyl lauroyl taurate, sodium methyl stearoyl taurate and sodium methyl palmitoyl taurate (and their analogues of different alkyl chain length), ammonium lauryl sulphate, ammonium laureth sulphate, sodium cocoyl sarcosinate, triethanolamine lauryl sulphate, triethanolamine laureth sulphate, disodium oleamide sulfosuccinate, disodium laureth sulfosuccinate, disodium dioctyl sulfosuccinate. Other classes of anionic surfactants which may be suitable include the alkaryl sulphonates, alkyl succinates, alkyl sulphosuccinates, N-alkoyl sarcosonates, alkyl phosphates, alkyl ether phosphates, alpha-olefin sulphonates and acyl methyl taurates, especially the sodium, magnesium, ammonium and mono-, di- and triethanolamine salts. Alkyl groups in the preceding may contain 8 to 20 carbon atoms. Alkyl ether sulphates and alkyl ether phosphates may contain 1 to 10 ethylene oxide or propylene oxide units per molecule.

A preferred combination of acidic polymer and anionic surfactant is Carbopol™ ETD 2020 or Gantrez™ S97, and sodium lauryl sulphate or an alpha-olefin sulphate anionic surfactant such as the commercial material Bioterge As-40 (a water soluble alpha-olefin surfactant which is stable at acid pH.

In one embodiment of the novel formulation of this invention the acidic polymer and the anionic surfactant are suitably present together in the solution in the ratio of weight % acidic polymer:anionic surfactant 1-2:2-1, suitably 1:1.5+/−0.2. Suitably in the solution the acidic polymer is present at 1-5, preferably 2+/−0.2, weight %, and the anionic surfactant at 0.1-4, preferably 1.5+/−0.2 weight %.

In another embodiment of the novel formulation of this invention, when the acidic polymer is of the above-mentioned type which includes adjacent

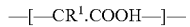

—[—$CR^1$.COOH—]— units (where $R^1$ is defined above) in its structure, for example the polymers based on maleic acid moieties which typically include —[—CH.COOH—CH.COOH—]— units, and/or salts or esters of such units, or including such units in anhydride form in which COOH groups on adjacent carbon atoms may be cyclised to form a

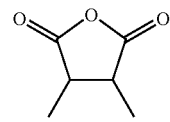

ring system, such as the above-mentioned polymers available commercially under the name Gantrez™, e.g. Gantrez™ S97, the acidic polymer and the anionic surfactant are suitably present together in the solution in the ratio of weight % acidic polymer:anionic surfactant 3:1-1:2. Suitably in the solution the acidic polymer is present at 1-7 weight %, and the anionic surfactant at 1-6, suitably 3+/−0.2 weight %.

The novel formulation of the invention is preferably at a pH in the range 2-4. This may for example be achieved using a suitable pH buffer in the solution. A suitable buffer may be provided by including one or more organic carboxylic acid, such as citric (which is preferred), salicylic, fumaric, benzoic, glutaric, lactic, malonic, acetic, glycolic, malic, adipic, succinic, aspartic, phthalic, tartaric, glutamic, pyroglutamic, or gluconic acid, or a mixture of two or more thereof. Additionally or alternatively a base such as sodium hydroxide, or a mineral acid such as hydrochloric acid may be included to achieved a pH at the suitable level.

A suitable liquid vehicle is an aqueous vehicle, e.g. water, or ethanol, or a mixture of ethanol and water. For example in such a mixture the ethanol:water ratio by volume may be in the range 4:1-1:1.5, typically 3:1-1:1.

The novel sanitising formulation of this invention may be in the form of a mobile liquid, or may alternatively be in the form of a viscous gel. For example it is found that the above-mentioned cross-linked poly-(carboxylic acid) polymers being homopolymers of acrylic acid crosslinked with an allyl ether, e.g. of pentaerythritol, of sucrose or of propylene, e.g. the material available from B.F. Goodrich Company under the trade name "Carbopol", such as the specific Carbopols include Carbopol 934, 940, 980, 1382, Carbopol ETD 2020, ETD 2050, Ultrez 20 and 21 tend to form a gel in combination with the anionic surfactant. The term "liquid" herein encompasses such a mobile gel. Such a gel may be advantageous in facilitating the dispensing of the sanitising formulation and its application to the skin.

In contrast the polymers comprising the unit:

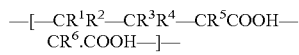

in its structure wherein $R^1$, $R^2$, $R^3$, $R^4$, $R^5$ and $R^6$ are independently hydrogen (preferred) or $C_{1-3}$ alkyl or $C_{1-3}$ alkoxy, preferably $R^1$ and $R^2$ being hydrogen, $R^3$ being hydrogen $R^4$ being methoxy, and $R^5$ and $R^6$ being hydrogen, or a derivative thereof retaining COOH groups in its structure, or groups readily hydrolysable to COOH groups, such as the above-mentioned polymers commercially available under the trade name Gantrez™ tend to remain as mobile liquids.

The formulation of the invention may contain other substances to enhance their effectiveness, to provide additional functions, or suitability for specific uses.

For example the formulation may contain one or more additional antimicrobial substances.

Citric acid is known to have antiviral activity, and when present in the formulation of the invention may perform this antiviral function in addition to a pH controlling function. Typically the formulation of the invention may include 0.5-7, typically 1-5+/−0.25 weight % of citric acid.

Preferred formulations of the invention therefore preferably comprise the acidic polymer, of the above-mentioned polycarboxylic acid type which includes adjacent

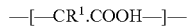

units (where $R^1$ is defined above) in its structure, for example polymers based on maleic acid moieties which typically include —[—CH.COOH—CH.COOH—]— units, and/or salts or esters of such units, or such units in anhydride form in which COOH groups on adjacent carbon atoms may be cyclised to form a

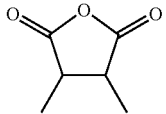

ring system, such derivatives being susceptible to hydrolysis to form the corresponding free acid, the anionic surfactant, and citric acid.

Therefore a preferred formulation of the invention comprises 1.5-0.5 weight % Gantrez™ S-97, 1-2 weight % of a sodium alkyl sulphate such as sodium lauryl sulphate, and 0.5-1.5 weight % citric acid.

Therefore another preferred formulation of the invention comprises 3.5-2.5 weight % Gantrez™ S-97, 6-4, preferably 4.5-5.5 weight % of an alpha-oelfinic sulphonate such as Bioterge As-40, and 2.5-1.5 weight % citric acid.

Other suitable antimicrobial substances include thymol (antifungal), triclosan, one or more sulphite salt such as sodium sulphite, one or more zinc salt such as zinc chloride, one or more alky or aryl ammonium salt known to have antimicrobial activity such as the commercial material Hyamine™ which comprises primarily dimethylbenzyl ammonium chloride, or BTC 2125 which comprises n-alkyl dimethyl benzyl ammonium chlorides and n-alkyl dimethyl-ethylbenzyl ammonium chlorides, triacetin (antifungal) and sorbic acid.

For example the formulation may contain one or more chelating substance such as the commercial material Versenol™.

For example the formulation may include a fluorescent marker e.g. which visibly glows under ultraviolet light and which is likely to remain on a surface to which it has been applied, so that compliance in use of the sanitising formulation, e.g. in a hospital environment can be checked. An example of such a fluorescent colorant is disodium distyryl-biphenyl disulphonate or 8-hydroxy-1,3,6-pyrenesulphonic acid trisodium salt (CI 59040).

Therefore a further aspect of this invention provides the use of the novel sanitising formulation for sanitising a surface, in particular a user's skin, in particular for sanitising such a surface contaminated or believed to be contaminated with potentially harmful microorganisms, e.g. bacteria or viruses.

In this use the formulation may be conventionally used by applying it to the surface or hands either per se e.g. poured or sprayed onto the surface, or the surface may be dipped into the formulation, or the formulation may be absorbed on e.g. a sponge, cloth or tissue etc. and applied to the surface using this.

In a fourth aspect of the invention the sanitising formulation herein is provided for use as a sanitising formulation for a surface, especially for use as a sanitising formulation for a user's skin, for example hands. For such use the formulation is preferably provided in a dispenser facilitating application to the surface, e.g. contained in a dispensing container, or in a refill for such a dispensing container. Typically for use as a sanitising formulation for the skin the novel formulation may be provided in a container provided with a hand-operable pump.

The formulations disclosed herein may be prepared by a conventional procedure of mixing together the ingredients e.g. the acidic polymer, pH buffer materials, anionic surfactant, other substances if present such as the UV fluorescent colourant, and the liquid vehicle, and agitating the mixture until all has dissolved. It is preferred to disperse the acidic polymer first in the liquid vehicle then to mix in the anionic polymer and other ingredients. The above order of addition of the ingredients may be important if the mixing of the acidic polymer and anionic surfactant may be expected to cause gelling of the mixture.

A further aspect of the invention provides a concentrate suitable for dilution with the liquid vehicle to thereby provide the sanitising formulation herein. Such a concentrate may comprise a mixture of the acidic polymer and the ionic surfactant, suitably in the weight % ratio range 1-2:2-1, preferably 1:1.5+/−0.2. Such a concentrate may also include materials such as one or more of the above-mentioned organic carboxylic acid and alkali such that the pH of the diluted made-up sanitising formulation has the desired pH e.g. 2-4.

Such a concentrate may be provided for use in a suitable container.

EXAMPLES

The present invention will now be described by way of example only.

Example 1

| | |
|---|---|
| Acidic polymer: | Carbopol ETD 2020 2% w/w |
| Surfactant: | Sodium Lauryl Sulphate 1.5% w/w |
| Organic carboxylic acid: | Citric Acid 1% w/w |
| pH Adjuster: | Sodium Hydroxide qs to pH 3 |
| | Water to 100% |

Example 2

| | |
|---|---|
| Acidic polymer: | Gantrez S97 1% w/w |
| Surfactant: | Sodium Lauryl Sulphate 1.5% w/w |
| Organic carboxylic acid: | Citric Acid 1% w/w |
| pH Adjuster: | Sodium Hydroxide qs to pH 3 |
| | Water to 100% |

Evaluation of In-Vitro Antimicrobial Efficacy.

Samples of the above sanitising formulations were assessed by suspension testing following the microbiological preservative efficacy test method described in the European Pharmacopoeia and United States Pharmacopoeia.

Organisms Used.

*Escherichia coli* NCIMB 8545

*Staphylococcus aureus* NCIMB 9518

Procedure.

4.5 ml of the formulation was combined with 0.5 ml of bacterial suspension ($10^7$CFU/ml). After 1 minute 1 ml of the mixed solution was removed and diluted with 9 ml of neutralisation media (Tryptone Soya Broth with 10% Tween 20 and 3% lecithin). Serial dilution was performed and 1 ml pour plate method used to count the number of survivors. Results were expressed as mean CFU/ml. Log reduction was calculated by comparing the initial log of the bacterial suspension prior to addition to the product with the value after 1 minute exposure.

Evaluation of In-Vitro Virucidal Activity.

Samples of the above sanitising formulations were assessed by the method described in ASTM E1052.

Virus Used.

Influenza A/Hong Kong 8/68 ATTC544/GBL 44540, pool #3 ref no 744-239-112

Procedure.

0.1 ml of organism was added to 0.9 ml of sample and left in contact for ten minutes at 20-25° C. The inoculated sample was diluted 10-1 to 10-6 in neutralising medium. Samples were assayed and the log reduction in virus titre calculated by comparing the initial value prior to addition of the product with the value after 10 minutes exposure.

Results.

| Sample | Influenza A Log Reduction@ 10 mins (EID50/0.1 ml) N = 4 | Log Reduction *S. Aureus* @ 1 min | Log reduction *E. Coli* @ 1 min |
|---|---|---|---|
| Example 1 | 5.5 | >5.5 | >5.5 |
| Example 2 | 5.5 | >5.5 | >5.5 |

Further examples of sanitizing solutions according to this invention are listed below.

Example 3

| | weight % |
|---|---|
| Gantrez S-97BF 13% solution | 23.10 |
| Bioterge As-40* | 5.00 |
| Citric Acid | 2.00 |
| Versenol 120** (41%) | 0.25 |
| Alcohol (Undenatured) 95% | 66.75 |
| Hydrochloric acid 0.5N | 1.40 |
| Triacetin | 1.50 |
| pH (as is) | 2.61 |
| Total | 100.00 |

*Bioterge As 40 is a sodium salt of alpha-olefin sulphonates which is stable at acid pH. The anionic content was used in the formulation.
**Versenol ™ 120 chelating agent is an aqueous solution of the trisodium salt of N-(hydroxyethyl) ethylenediaminetriacetic acid.

Example 4

| | weight % |
|---|---|
| Gantrez S-97BF 13% solution | 23.10 |
| Bioterge As-40 | 5.00 |
| Citric Acid | 2.00 |
| Versenol 120 (41%) | 0.25 |
| Alcohol (Undenatured) 95% | 63.40 |
| Zinc chloride | 0.25 |
| Sodium hydroxide 0.5N | 4.50 |
| Triacetin | 1.50 |
| pH (as is) | 2.60 |
| Total | 100.00 |

The anionic content was used in the formulation

The invention claimed is:

1. An alcohol-free sanitizing formulation having anti-viral activity comprising a solution of 1-5 wt % of an acidic polymer comprising a homopolymer of acrylic acid crosslinked with an allyl ether, 1-5 wt % of an anionic surfactant, and 0.5-7 wt % of citric acid made up to 100% with water, at pH 2-4, wherein the acidic polymer and anionic surfactant interact to form a viscous gel.

2. The sanitizing formulation according to claim 1 wherein the acidic polymer comprises a homopolymer of acrylic acid crosslinked with an allyl ether of pentaerythritol, of sucrose or of propylene.

3. The sanitizing formulation according to claim 2 wherein the acidic polymer comprises Carbopol ETD 2020.

4. The sanitizing formulation according to claim 1 wherein the anionic surfactant is a compound having a hydrophilic anionic group and an associated cation.

5. The sanitizing formulation according to claim 4 wherein the anionic surfactant is selected from sodium lauryl sulphate, sodium laureth sulphate, and alpha-olefin sulphates.

6. The sanitizing formulation according to claim 5 comprising Carbopol™ ETD 2020 and sodium lauryl sulphate or an alpha-olefin sulphate.

7. The sanitizing formulation according to claim 1 wherein the acidic polymer and the anionic surfactant are present together in the solution in the ratio of weight % acidic polymer:anionic surfactant 1-2:2-1.

8. The sanitizing formulation according to claim 1 provided for use as a sanitizing formulation for a surface.

9. A concentrate suitable for dilution with a liquid vehicle to thereby provide a sanitizing formulation as claimed in claim 1.

10. A sanitising formulation according to claim 1 having anti-viral activity consisting of a solution of 1-5 wt % of an acidic polymer comprising a homopolymer of acrylic acid crosslinked with an allyl ether, 1-5 wt % of an anionic surfactant, and 0.5-7 wt % of citric acid made up to 100% with water, at pH 2-4, wherein the acidic polymer and the anionic surfactant interact to form a viscous gel.

* * * * *